United States Patent [19]

Hennings

[11] 4,068,661
[45] Jan. 17, 1978

[54] INJECTION SYRINGE WITH SEPARATE ONE-PIECE FINGER REST

[75] Inventor: Werner Hennings, Bunde, Germany

[73] Assignee: Bunder Glas GmbH, Germany

[21] Appl. No.: 656,461

[22] Filed: Feb. 9, 1976

[30] Foreign Application Priority Data

Feb. 12, 1975 Germany .................. 7504229[U]

[51] Int. Cl.² ............................................. A61M 5/00
[52] U.S. Cl. ................................. 128/215; 128/218 R
[58] Field of Search ............... 128/215, 218 R, 218 D, 128/218 N, 220, 221, 234, 216

[56] References Cited

U.S. PATENT DOCUMENTS

| | | | |
|---|---|---|---|
| 1,331,805 | 2/1920 | Chance | 128/218 R |
| 1,712,084 | 5/1929 | Kulik | 128/218 R |
| 1,752,384 | 4/1930 | Jamison | 128/218 D |
| 1,832,533 | 11/1931 | Creasy | 128/218 R |
| 1,950,137 | 3/1934 | Dowe | 128/220 |
| 2,512,882 | 6/1950 | Truesdale | 128/215 |
| 3,921,633 | 11/1975 | Tischlinger | 128/215 X |

Primary Examiner—John D. Yasko
Attorney, Agent, or Firm—Lowe, King, Price & Markva

[57] ABSTRACT

An injection syringe comprises a cylindrical barrel provided at its open rear end with an initially separate one-piece finger rest and at its forward end with an inserted or permanently fitted cannula or with a conical fitting for the subsequent fixing of a cannula, and a plunger which closes the open rear end of the barrel and which is slidably displaceable inside the barrel by a ram. The barrel of the syringe is formed at its forward end with a head of any desired kind and is provided at its open rear end either in its external or its internal cylindrical surface with one or more annular or similarly shaped recesses or grooves. The peripheral inside or outside surface of the finger rest is formed with a corresponding number of projecting ridges which may be in the form of arcuate ridge segments. These ridges or ridge segments are complementary to the recesses or grooves in the barrel in such a way that when the finger rest is fitted to the barrel the ridges or ridge segments on the finger rest engage the recesses or grooves in the barrel.

5 Claims, 3 Drawing Figures

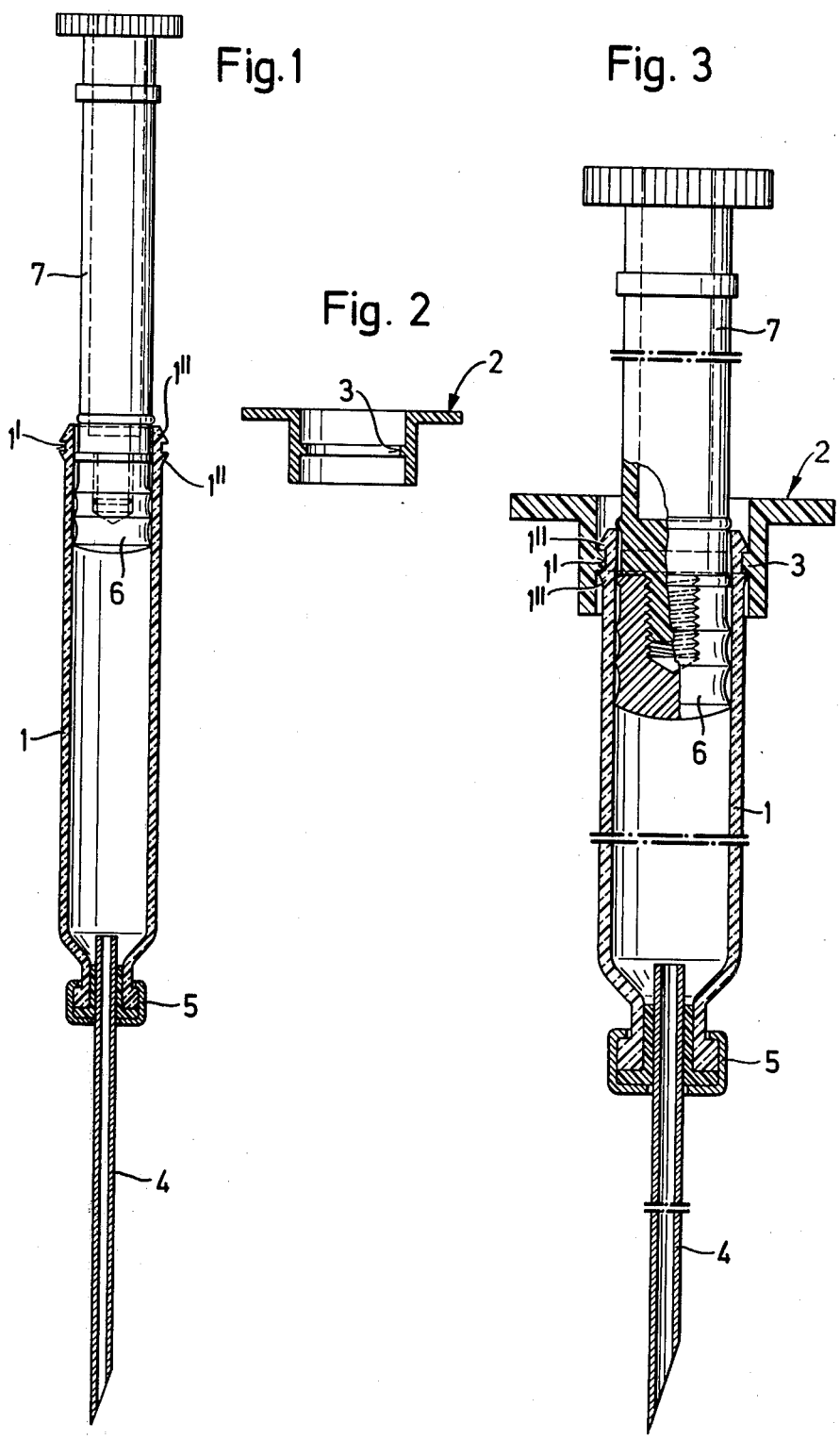

INJECTION SYRINGE WITH SEPARATE ONE-PIECE FINGER REST

BACKGROUND OF THE INVENTION

This invention relates generally to injection syringes comprising a cylindrical barrel provided at its open rear end with a finger rest region where a finger rest is disposed. An inserted or permanently fitted cannula or a conical fitting for the subsequent fixing of a cannula is located at the forward end of the barrel. A plunger closes the open rear end of the barrel and is slidably displaceable by a ram.

Such injection syringes are used in medical practice for the administration of injectants subcutaneously, intramuscularly, intravenously or in other conventional ways.

Generally, these syringes are made of glass and sometimes or synthetic plastics. Their principal functional parts are the barrel which serves for the reception of the injectant in liquid or solid form, and the plunger which can be moved from the outside by the ram to displace the injectant through the outlet opening in the barrel neck or through a terminal fitting into the body by a cannula.

As is well understood such an injection syringe is manipulated with one hand and must therefore be provided with a surface for applying pressure with the thumb and with a finger rest for the index and middle fingers of the operator's hand.

This finger rest is a component which is either integrally formed with the barrel of the syringe or separate therefrom and adapted to be fitted over the end of the barrel and to be thus secured. In such a case the finger rest need not be made of glass like the barrel of the syringe, instead of which it may consist of a synthetic plastics or some other suitable material.

For ensuring that the separate finger rest is a firm fit, a known practice is to form a projecting ring on the end of the barrel of the syringe. However, the presence of such a projecting ring is open to the objection that conventional machines are unsuitable for producing and further working a syringe with a barrel of such a kind. The attachment of a finger rest to the cylindrical barrel having a projecting ring requires special machines which significantly raises the cost of production.

SUMMARY OF THE INVENTION

It is therefore an object of the invention to provide an injection syringe to which a separately produced finger rest can be attached in such a way that mostly conventional automatic machines can be used for the production and further working of the barrel of the syringe.

To attain this object, the present invention provides an injection syringe which comprises a cylindrical barrel having a forward end forming a head and an open rear end. The barrel has a finger rest region in the vicinity of its open rear end with at least one annular groove. A cannula is held by the head. A plunger closes the open rear end of the barrel. A ram slidably displaces the plunger inside the barrel. An initially separate one-piece finger rest formed with at least one ridge which is complementary to the groove in the barrel in such a way that when the finger rest is fitted to the barrel the ridge on the finger rest engages the groove in the barrel.

The cross section of the ridge on the finger rest preferably matches the cross section of the groove in the barrel of the syringe.

On each side of the groove the barrel may be formed with an annular thickening ridge for the purpose of achieving a snap action effect when the separate finger rest is fitted to the barrel.

The barrel and the finger rest of the assembled syringe may consist of the same or of different materials, such as glass, synthetic plastics or metal.

BRIEF DESCRIPTION OF THE DRAWING

An embodiment of the invention will now be described by way of example and with reference to the accompanying drawing, in which:

FIG. 1 is an elevational view, partly in section, of an injection syringe according to the invention, ready for use, but not yet provided with a finger rest;

FIG. 2 is a section of an initially separate finger rest, and

FIG. 3 is a view similar to that shown in FIG. 1 but showing the complete injection syringe after having been provided with the finger rest.

DESCRIPTION OF THE PREFERRED EMBODIMENT

The shape of an integrally formed head on the cylindrical barrel 1 of a syringe will be clear from an inspection of FIGS. 1 and 3. A cannula 4 is inserted into this head by having been passed through a cap member 5 and located by a sealing bush in the necked forward end of the barrel of the syringe.

Instead of the cannula 4 being secured in the head of the barrel as described, the head may also be provided with a conical fitting for the subsequent insertion of a cannula. Such a fitting might advantageously consist of an aluminum cap, a rubber washer and a conical member embraced by a separate thimble type seal.

The rear end of the barrel 1 of the syringe is open and, as illustrated in FIGS. 1 and 3, slidably contains a plunger 6 which maintains sealing contact with the inside surface of the barrel, being formed of a plurality of discs. The plunger 6 is provided with internal threads which enable it to be detachably affixed to a hollow ram 7. When the syringe is not in use this hollow ram 7 may serve for accommodating the cannula 4.

FIG. 2 illustrates an initially separate one-piece finger rest 2. This rest consists of a cylindrical body having one or more radial extensions at one end. These extensions provide surfaces which can be gripped by the index and middle fingers. Internally the cylindrical body contains a mating surface having an annular ridge 3 which might be divided into a number of parts forming arcuate ridge segments.

This finger rest 2 is pushed over the open rear end of the cylindrical barrel 1 of the syringe on which it is retained in the required position. This is because the annular ridge 3 or the ridge segments snap into engagement with annular groove 1' provided in a finger rest region on the outside surface of the barrel 1 in the vicinity of the open rear end thereof (see FIG. 1). The dimensions of the annular groove 1' and of the annular ridge 3 are so matched that when in engagement the finger rest 2 will be firmly located. In other words, the mating surface of the finger rest 2 is correspondingly shaped with respect to the shape of the finger rest region on the outside surface of the barrel 1. It is self-evident that instead of one ridge and one groove two or more ridges 3 and grooves 1' may be provided.

In order to improve the reliability with which the finger rest 2 is located and held on the open end of the barrel 1 and in order to achieve a reliable snap action effect the wall of the barrel, as shown at 1", on each side of the annular groove 1' is slightly thickened. The thickening ridges 1" thus formed slightly increase the external diameter of the cylindrical barrel 1 of the syringe. In this context it may be observed that the deformation of the outside surface of the barrel 1 will be accompanied by a slight constriction of the internal cross section of the precisely cylindrical part, and that advantage can be taken of this constriction for braking the plunger. With the same end in view a small ring of a diameter slightly exceeding the internal diameter of the barrel 1 may be mounted on the ram 7 to the rear of the threaded end of the ram. After the resistance due to the inward constriction of the barrel 1 due to its deformation has been overcome the plunger 6 can be easily pushed forwards. When the plunger 6 is retracted the ring on the ram 7 has a braking effect and prevents the plunger 6 from being pulled out of the barrel otherwise than by the application of some force.

In a different arrangement of the barrel this is provided with recesses or annular grooves on its inside surface. Part of the finger rest is in such case inserted into the barrel, the ridges or arcuate ridge segments being in such a case situated on the external peripheral surface of this part of the finger rest. After having been forced into position the finger rest will then form an additional stop for the plunger 6 when drawing in the injectant or an additional preparation.

The advantage achieved over conventional arrangements is that the barrel 1 of the syringe can be handled by conventional machines without the need of additional devices, such as are required for barrels having projection flanges for the retention of the finger rest.

It is also an advantage that by reason of its particular design the finger rest is satisfactorily located on or in the barrel of the syringe without requiring the use of special aids, such as adhesives, hot air or the like for its affixation.

With reference to the finger rest it should be noted that its inside may be so constructed that the snap action effect is obtained both when the finger rest is fitted by pushing it on over the head end of the barrel or over the rear end which is closed by the plunger.

A not insignificant advantage is the generation of the braking effect on the plunger. The proposed design admits of diverse modifications, as will be readily understood.

Yet another advantage is that the production cost is substantially lower than that of conventional syringes.

Hence the injection syringe proposed by the invention may be regarded as a one-way article, i.e. as an expendable article.

The invention may be embodied in other specific forms without departing from the spirit or essential characteristics thereof. The embodiment is therefore to be considered in all respects as illustrative and not restrictive.

What is claimed is:

1. An injection syringe comprising:
   a. a cylindrical barrel having a forward end forming a head and an open rear end;
   b. the barrel having a finger rest region in the vicinity of its open rear end with at least one annular groove;
   c. a cannula held by the head;
   d. a plunger closing the open rear end of the barrel;
   e. a ram for slidably displacing the plunger inside the barrel;
   f. an initially separate, one-piece finger rest having a mating surface that is correspondingly shaped with respect to the shape of said finger rest region and includes at least one ridge which is complementary to the groove in the barrel;
   g. the finger rest being slidingly fitted to the barrel with the ridge on the finger rest being effective to engage the groove in the barrel and secure the finger rest in place; and
   h. an annular thickening ridge is located on each side of said groove in the barrel to create a snap action effect when the separate finger rest is fitted to the barrel.

2. An injection syringe as defined in claim 1, wherein the head of the barrel (1) comprises a cap member (5) in which the cannula is inserted and located by a sealing bush.

3. An injection syringe as defined in claim 1, wherein the groove is provided in the outside surface of the barrel and the ridge is provided on the inside surface of the finger rest.

4. An injection syringe comprising:
   a. a cylindrical barrel having a forward end forming a head and an open rear end;
   b. the barrel having an outside surface with a finger rest region in the vicinity of its open rear end with at least one annular groove;
   c. a cannula held by the head;
   d. a plunger closing the open rear end of the barrel;
   e. a ram for slidably displacing the plunger inside the barrel; and
   f. an initially separate, one-piece finger rest having an inside surface with a mating surface that is correspondingly shaped with respect to the shape of said finger rest region and includes at least one ridge which is complementary to the groove in the barrel;
   g. the finger rest being slidingly fitted to the barrel with the ridge on the finger rest being effective to engage the groove in the barrel and secure the finger rest in place;
   h. the barrel includes an annular thickening ridge on each side of its groove to create a snap action effect when the finger rest is pressfitted to the barrel;
   i. said barrel being made of a material such that deformation of the outside of the barrel is accompanied by a constriction of the internal cross section of the precisely cylindrical barrel.

5. An injection syringe as defined in claim 4, wherein the ram includes a ring of a diameter slightly exceeding the internal diameter of the barrel, said ring being mounted to the rear of the threaded end of the ram.

* * * * *